United States Patent [19]

Green et al.

[11] Patent Number: 5,591,977
[45] Date of Patent: Jan. 7, 1997

[54] VARIABLE AXIAL APERTURE POSITRON EMISSION TOMOGRAPHY SCANNER

[75] Inventors: Michael V. Green, Kensington; Jurgen Seidel, Bethesda; William R. Gandler, Rockville, all of Md.

[73] Assignee: The United States of America as represented by the Secretary of the Department of Health and Human Services, Washington, D.C.

[21] Appl. No.: 357,574

[22] Filed: Dec. 15, 1994

Related U.S. Application Data

[63] Continuation-in-part of Ser. No. 235,310, Apr. 29, 1994, abandoned.

[51] Int. Cl.$^6$ .................................................. G01T 1/166
[52] U.S. Cl. ........................ 250/363.03; 250/363.04; 250/363.05
[58] Field of Search ..................... 250/363.03, 363.04, 250/363.05, 363.08

[56] References Cited

U.S. PATENT DOCUMENTS

| | | | |
|---|---|---|---|
| H12 | 1/1986 | Bennett et al. | 250/363.03 |
| 3,431,413 | 3/1969 | Anderson et al. | 250/363.02 |
| 4,180,736 | 12/1979 | Goodman | 250/363.01 |
| 4,298,800 | 11/1981 | Goldman | 250/369 |
| 4,362,946 | 12/1982 | Cusano et al. | 250/483.1 |
| 4,419,763 | 12/1983 | Hawman | 378/149 |
| 4,511,799 | 4/1985 | Bjorkholm | 250/367 |
| 4,652,759 | 3/1987 | Platz . | |
| 5,206,512 | 4/1993 | Iwao | 250/363.04 |
| 5,349,190 | 9/1994 | Hines et al. | 250/363.05 |

FOREIGN PATENT DOCUMENTS

| 0517601 | 12/1992 | European Pat. Off. . | |
|---|---|---|---|
| 171130 | 7/1991 | Japan | 250/363.1 |

*Primary Examiner*—Carolyn E. Fields
*Attorney, Agent, or Firm*—Lowe, Price, LeBlanc & Becker

[57] ABSTRACT

An imaging device includes a means for defining an imaging target space and at least two scintillation cameras which are positioned on opposite sides of the imaging target space so as to define one or more matched pairs of scintillation cameras. Each of the scintillation cameras includes a scintillation crystal. Means are provided for tilting the scintillation cameras of the one or more matched pairs of scintillation cameras and their respective scintillation crystals, so as to maximize coincidence detection sensitivity by adjusting an axial field of view to match an axial extent of a target located in the imaging target space. Means for processing signals generated by the scintillation cameras are also provided. Each pair of cameras is configured to detect paired gamma rays, emitted simultaneously and in opposite directions from a point of annihilation of a positron in the target within the target space, to thereby define endpoints of a coincidence line passing through the target and connecting the pair of cameras. Each pair of cameras generates electrical signals, responsive to substantially simultaneous absorption of each of the paired gamma rays by a respective one of the pair of cameras, indicative of the paired gamma rays emanating from a single positron annihilation in the target.

19 Claims, 5 Drawing Sheets

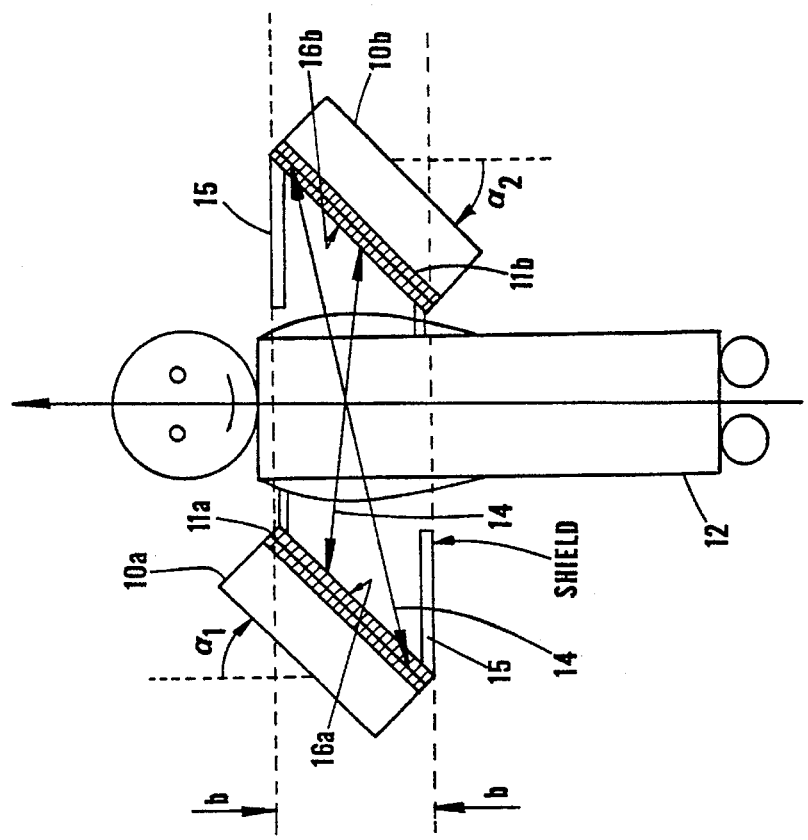
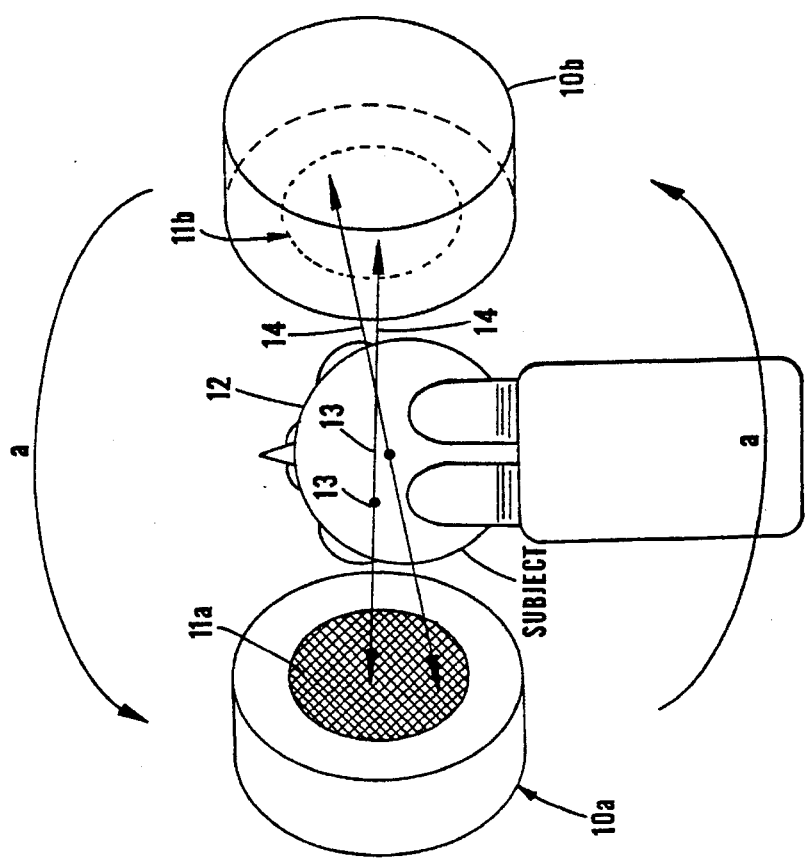
Figure 1a
Figure 1b

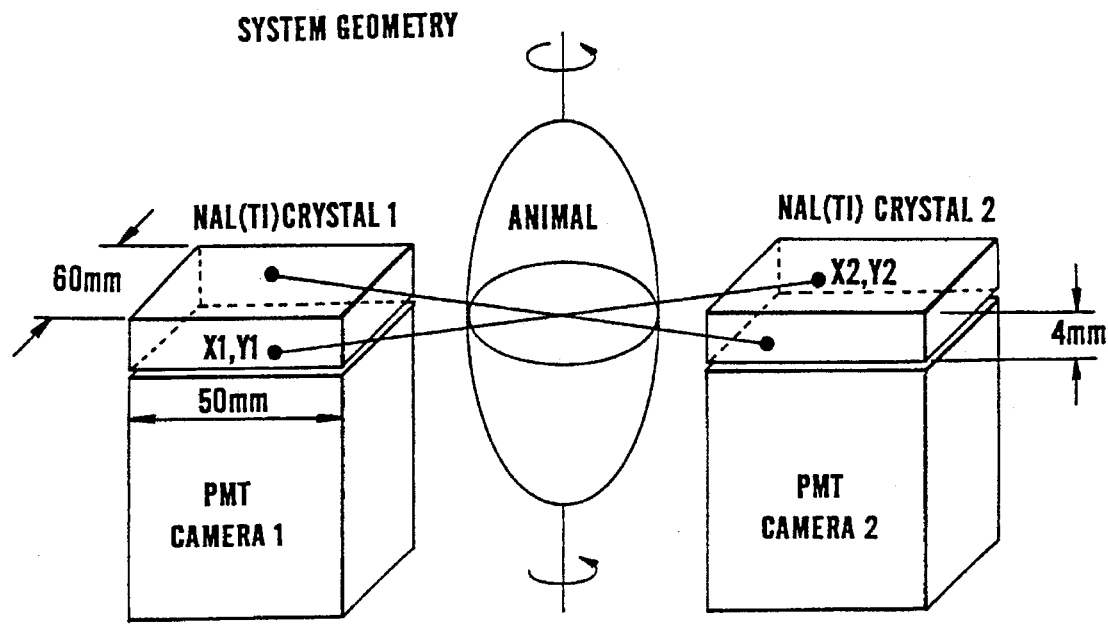
Figure 3
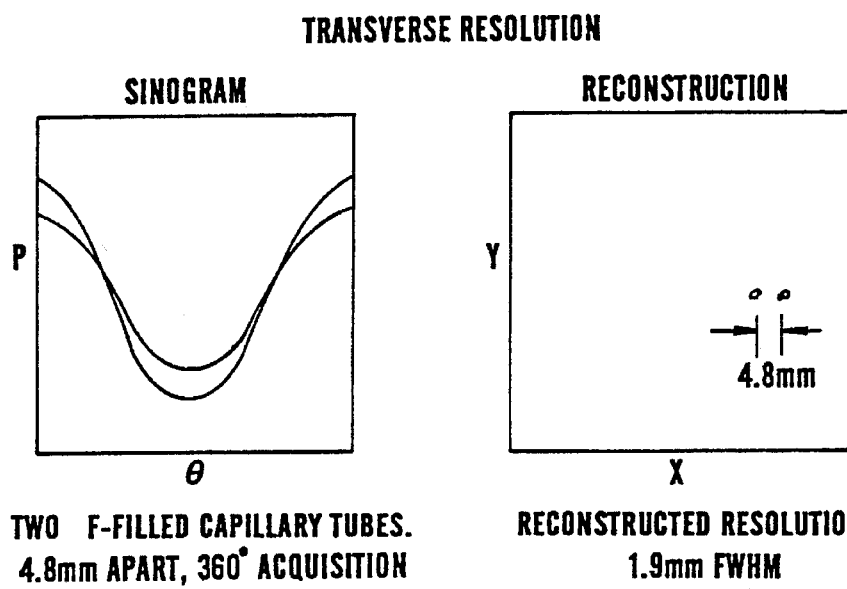
Figure 4a
Figure 4b

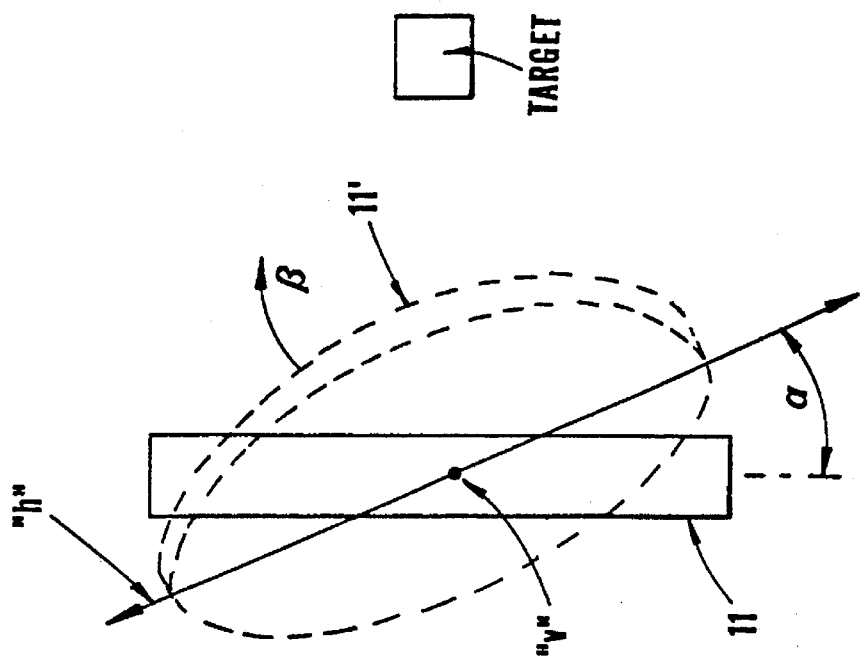
Figure 6b
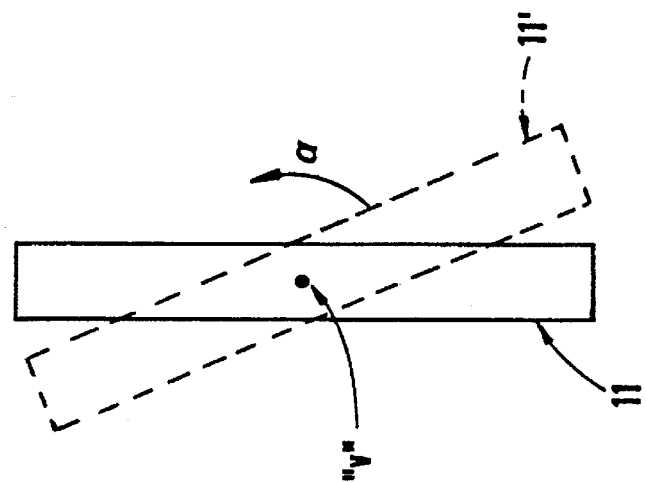
Figure 6a
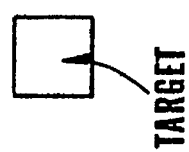

VARIABLE AXIAL APERTURE POSITRON EMISSION TOMOGRAPHY SCANNER

RELATED APPLICATIONS

This application is a continuation-in-part of U.S. patent application Ser. No. 08/235,310, filed Apr. 29, 1994, now abandoned, the entire disclosure of which is incorporated by reference.

TECHNICAL FIELD

The present invention relates to gamma ray imaging devices which employ scintillation cameras. More particularly, the present invention relates to gamma ray imaging devices which are capable of imaging distributions of single photon and positron emitting tracers in the body.

BACKGROUND ART

The scintillation camera has been the standard single photon imaging device in nuclear medicine for more than 25 years. This device, originally invented by Hal O. Anger in the late 1950's, has been continuously refined and improved since it was first developed. Contemporary scintillation cameras exhibit high levels of performance as compared to earlier models.

More recently, scintillation imaging systems have been adapted to single photon emission computed tomography (SPECT). This procedure usually involves rotating one or more scintillation cameras around a subject to obtain projection images which are required for tomographic reconstruction of the internal radioactivity distribution. These systems are now in use for both planar projection imaging and for SPECT in nuclear medicine clinics worldwide.

For about the last decade or so an alternative method to single photon imaging with the scintillation camera has received increasing academic and commercial attention, positron emission tomography (PET). According to this technique, positron emitting radioisotopes are attached to a desired tracer compound, administered to the patient and then imaged tomographically. The annihilation of a positron by a normal electron in the body gives rise to two simultaneous 511 keV gamma rays traveling nearly directly away from each other along the same line. Simultaneous detection of these two gamma rays (usually) by rings of detectors around the body defines the projection line along which the annihilation site must lie. The set of all such lines can be sorted into projection sets and these sets reconstructed tomographically to yield the internal activity distribution that gave rise to the projection sets. PET systems based on this "ring" design are considered to be the current state of the art.

Despite the sophistication of this design, ring machines possess a number of limitations: spatial resolutions better than 2 mm are difficult to achieve, thereby precluding use of such systems in small animal studies or in high resolution human studies; spatial resolution varies appreciably from the center to the edge of the field of view due to a depth of interaction effect and so on. Of perhaps greater importance, PET ring scanners are not capable of single photon imaging. On the other hand, scintillation cameras of conventional design are generally believed to be incapable of effective PET imaging. Thus, at present, there is no system believed capable of both forms of imaging.

The present invention is directed to an imaging system that is capable of both single photon imaging and positron emission tomography.

DISCLOSURE OF THE INVENTION

It is accordingly one object of the present invention to provide a multi-purpose gamma ray imaging device which can perform single photon planar imaging, single photon emission computed tomography, and positron emission tomography.

It is another object of the present invention to provide a multi-purpose imaging device which can be adjusted to match the axial length of the imaging target, thereby maximizing slice sensitivity.

A further object of the present invention is to provide a multi-purpose imaging device which includes one or more pairs of pivotable or tiltable scintillation cameras rotating about a target or a set of pivoted or tilted stationary cameras surrounding a rotating target.

A further object of the present invention is to provide a method of imaging which efficiently detects gamma rays at typical single photon energies (<200 keV) and at the high gamma ray energy associated with positron annihilation (511 kev).

A still further object of the present invention is to provide a method of imaging which embodies properties superior to the current state of the art in PET. In particular, the method can achieve a higher spatial resolution and improved spatial resolution uniformity compared to conventional PET, and a higher slice sensitivity than might be otherwise attained with a pair of opposed scintillation cameras operated in time coincidence.

According to these and further objects of the present invention which will become apparent as the description thereof proceeds, the present invention provides a multi-purpose gamma ray imaging device capable, when using collimation, of single photon planar imaging and single photon emission computed tomography and, when configured as described below, capable of positron emission tomography and that comprises:

means defining an imaging target space;

at least two scintillation cameras which are positioned on opposite sides of the imaging target space so as to define at least one matched pair of scintillation cameras, each of the at least two scintillation cameras including a scintillation crystal;

means for tilting or pivoting at least one of the at least two matched pair of scintillation cameras; and means for processing signals generated by the at least two scintillation cameras.

The present invention further provides for an imaging method which involves:

providing an imaging target space;

positioning a target capable of emitting gamma rays in said imaging target space;

positioning at least two scintillation cameras on opposite sides of said imaging target space, each of said at least two scintillation cameras including a scintillation crystal which produces an energy signal when a gamma ray is absorbed therein;

tilting or pivoting at least one of said at least two scintillation cameras so as to maximize tomographic slice sensitivity by adjusting an axial field of view to match an axial extent of the imaging target; and processing signals generated by said at least two scintillation cameras to produce an image of said target.

BRIEF DESCRIPTION OF DRAWINGS

The PET embodiment of the present invention will be described with reference to the attached drawings which are given by way of non-limiting examples only, in which:

FIG. 1a is a schematic representation of an end view of an imaging system according to one PET embodiment which shows a patient in a supine position with a pair of scintillation cameras positioned on either side of the patient.

FIG. 1b is a schematic representation of a top view of the imaging system of FIG. 1a.

FIG. 3 is a schematic illustration of another PET embodiment of the imaging system, paired stationary scintillation cameras arranged with coplanar scintillation crystals and the subject rotated between the cameras.

FIGS. 4a and 4b, respectively, show a sinogram of two parallel F-18 filled capillary tubes acquired with the imaging system shown in FIG. 3 and the reconstructed transverse (in-plane) resolution thereof. These figures collectively demonstrate the transverse resolution characteristics of this particular embodiment (single-slice PET mode, tilt angle=90 degrees)

FIG. 6a is a schematic top view illustrating the manner in which a scintillation crystal is tilted according to the present invention.

FIG. 6b is a schematic top view illustrating the manner in which a scintillation crystal is pivoted according to the present invention.

BEST MODE FOR CARRYING OUT THE INVENTION

Figure 2:
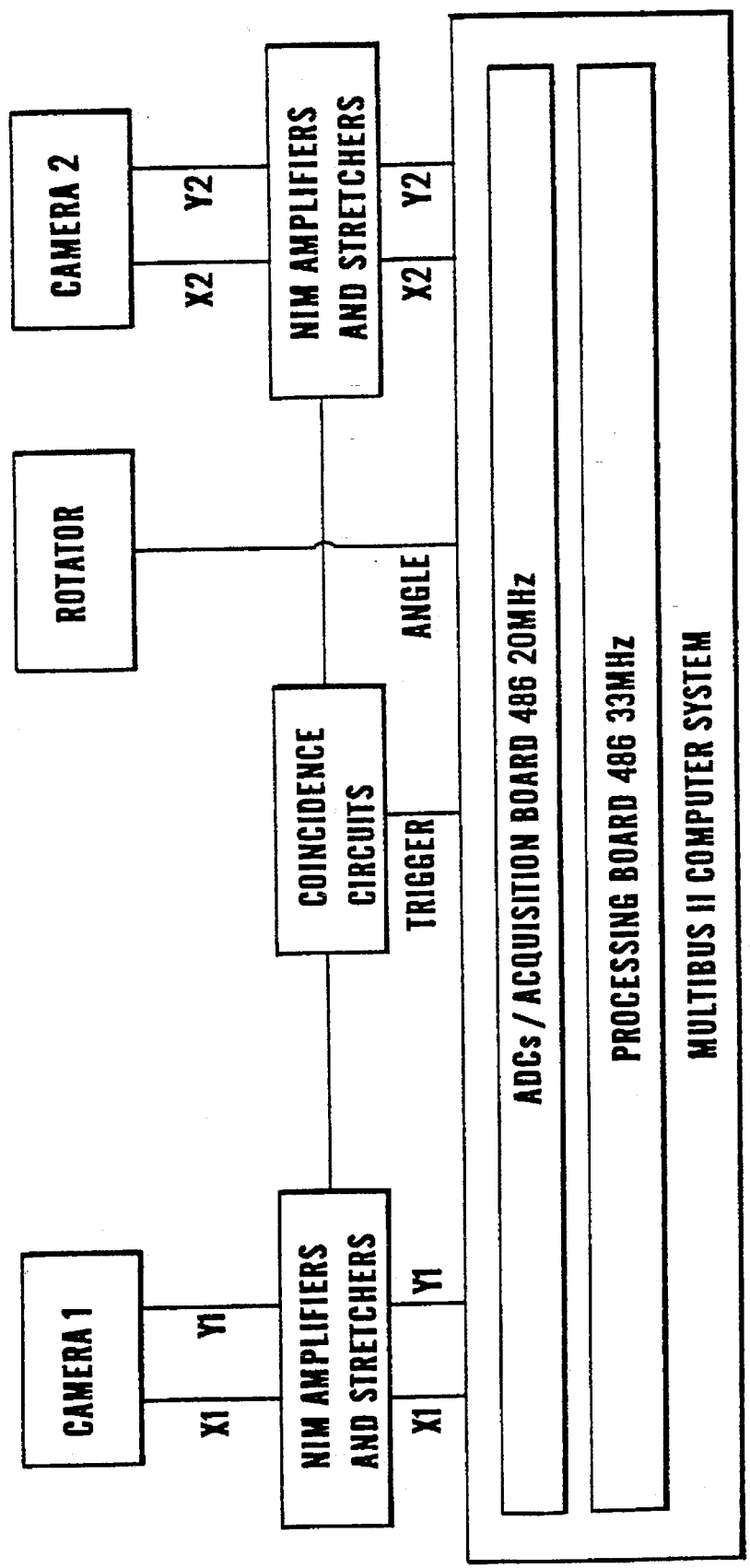
FIG. 2 is a schematic illustration of the data acquisition system used to service the two-camera PET embodiment shown in FIG. 1.

The present invention provides a multi-purpose gamma ray imaging system capable of all forms of nuclear tracer imaging including: single photon planar imaging, single photon emission computed tomography, and positron emission tomography. The present device can perform all of these tasks by a geometric reconfiguration of the two (or more) detector elements and, when operated in the PET mode, by placing the (one or more pairs of) detectors in time coincidence. The device, therefore, has application in both small animal imaging and as a high resolution human scanner with similar capabilities.

Recognizing that planar imaging and SPECT imaging with scintillation cameras are already well established, the inventors of the present invention have devised a way to use two (or more) moving or, potentially, stationary, scintillation cameras to perform high resolution, enhanced sensitivity PET imaging studies.

Several significant advantages are provided by the system of the present invention. For example, since the system is based on conventional scintillation cameras already capable of SPECT and planar imaging, the system can readily be used for routine and common clinical imaging procedures that constitute, by far, the bulk of the practice of nuclear medicine. Thus, the system satisfies the direct clinical needs of a nuclear medicine department. Because the system is capable of PET imaging, it allows for a major increase in diagnostic capabilities for a relatively modest increment in cost. In this regard, conventional multi-ring PET scanners can cost between 1 and 3 million dollars and are limited only to positron imaging. Currently, PET scanners must be purchased as a separate add-on to other imaging equipment, often at a prohibitive amount considering the other components required to perform PET, e.g. a cyclotron and radiochemistry facility. A general purpose system, according to the present invention could reduce the total instrument cost to perhaps less than a million dollars and enhance the use of both PET and SPECT technologies in clinical practice.

The present invention is based on the well-developed technology embodied in the scintillation camera. In this regard, the conventional scintillation camera has been optimized to image, by collimation, relatively low energy gamma rays by single photon emitting radioisotopes that have an energy level of usually less than 200 keV. This optimization is achieved by a number of strategies including reducing the thickness of the scintillation crystal. While this strategy is useful for low energy emitters, gamma rays from positron annihilation events are always 511 keV emissions, a much higher energy than usually encountered in single photon studies.

Because of the relatively thin sodium iodide crystals used in conventional scintillation cameras, the ability to stop, or detect, 511 keV radiation is poor. Therefore, the sensitivity of conventional scintillation cameras for 511 keV radiation events is considered unsatisfactory for imaging positron emitters.

The sensitivity of a scintillation camera can, however, be effectively increased to achieve PET scanning by increasing the thickness of the NaI crystals. This, in fact, has been done by workers at the University of Pennsylvania (Karp et al, "Continuous-Slice PENN-PET: A Positron Tomographic with Volume Imaging Capability", Journal of Nuclear Medicine, Vol. 31, No. 4, pp. 617–627 (May, 1990)). However, once the thickness of the NaI crystals is increased, the resulting system is no longer suitable for single photon imaging.

Conventional scintillation cameras already possess a high intrinsic spatial resolution at modest photon energies. Accordingly, the present inventors had to solve the problem of creating a usable PET scanner from a scintillation camera by somehow improving the detection efficiency of the system at 511 keV without compromising other aspects of the camera's performance that are advantageous in the low energy regime.

FIG. 1a is a schematic representation of an end view of an imaging system according to one embodiment of the present invention which shows a patient in a supine position with a pair of scintillation cameras positioned on either side of the patient. FIG. 1b is a schematic representation of a top view of the imaging system of FIG. 1a.

In FIGS. 1a and 1b, a pair of scintillation cameras 10a and 10b are positioned on either side of a subject 12 to be imaged so that faces 16a and 16b (see FIG. 1b) of the scintillation crystals 11a and 11b are substantially parallel and scintillation crystals 11a and 11b are in the same plane or coplanar so that the scintillation crystals 11a and 11b can receive gamma rays emitted from an internal area within the subject at position 13. In this manner, simultaneous scintillation events in each crystal define the endpoints of the line of flight 14 of annihilation photons produced within the subject.

The arrows "a" in FIG. 1a depict one manner in which the camera pairs 10a and 10b can, in one embodiment, be rotated about the subject 12 to collect samples of all such coincidence lines in order to allow the internal activity distribution to be reconstructed. This manner of rotating the cameras is conventional (in SPECT imaging) and therefore can be accomplished by known means. Reconstruction is also possible by acquiring endpoints from a ring of stationary cameras provided that these cameras completely "fill-in", or can by movement, be made to fill-in the space around the subject.

FIG. 1b illustrates one manner in which cameras 10a and 10b and their respective crystals 11a and 11b can be rotated so that the faces 16a and 16b of scintillation crystals 11a and 11b remain substantially parallel to one another while they are tilted. In FIG. 1b, the angle at which cameras 10a and 10b and their respective crystals 11a and 11b are tilted are identified by angles $\alpha_1$ and $\alpha_2$ which are equal, according to one embodiment of the invention. As the scintillation crystals 11a and 11b are tilted, there is a corresponding change in the field of view of the cameras 10a and 10b which is identified by the arrows "b" at the left in FIG. 1b. The field of view of the cameras 10a and 10b can be further controlled by adjusting shields 15.

In reference to FIG. 1b it is to be understood that the cameras 10a and 10b and their respective crystals 11a and 11b can be tilted together so that each of angles $\alpha_1$ and $\alpha_2$ can range from 0° to 90° as illustrated. This means that the scintillation crystals 11a and 11b can be tilted so that they either face each other or, at the other extreme, are coplanar with one another.

As shown in FIGS. 1a and 1b, the imaging system of the present invention includes two (or more) NaI(T1) scintillation cameras arranged geometrically such that faces 16a and 16b (see FIG. 1b) of the scintillation crystals 11a and 11b are substantially parallel and scintillation crystals 11a and 11b are in the same plane or coplanar. In this geometry, 511 keV photons from a source placed between the detectors enters the scintillation crystals at an oblique or shallow angle which is dependent on the tilt angle of the cameras relative to their rotation axis. In FIGS. 1a and 1b, two tilted detectors are shown that continuously or stepwise rotate around the subject, to acquire all possible coincidence lines.

Although two cameras are shown in FIGS. 1a and 1b for illustrative purposes, it is to be understood that more than two cameras could be used. If more than two cameras are used, each camera can be put into time coincidence with an opposite camera as shown or with several opposite cameras depending on their number and arrangement, thereby increasing sensitivity still further.

It should also be understood that the cameras may be tilted in a manner different from that shown in FIG. 1a and 1b, but for the same purpose. That is, rather than both cameras being at an angle $\alpha$ with respect to the rotation axis, one camera could be placed at an angle of $-\alpha$. That is, the cameras could be tilted toward or away from one another. In this mode, path length through the scintillation crystals is also increased but the system will possess a different sensitivity response than when in the parallel crystal mode of operation. In some circumstances, this configuration may be more advantageous than the parallel crystal configuration.

In practice, it has been determined that it is not necessary to tilt each scintillation crystal. In this regard, only one of the scintillation crystals can be tilted while the other remains fixed or stationary. It has also been determined that the tilt angles of the scintillation crystals do not have to be of equal magnitude. However, it is necessary that the scintillation crystals be positioned, i.e. tilted, so that they simultaneously receive charged gamma rays emitted from a target subject located between the scintillation crystals in order to identify end points of the line of flight of gamma rays produced by annilation events.

According to preferred embodiments of the present invention, the scintillation cameras and their respective scintillation crystals are "tilted" about a linear axis as depicted in FIGS. 1a and 1b. It is also possible according to further embodiments of the present invention to "pivot" the scintillation cameras and their respective scintillation crystals about a central point, e.g. the centroid, of each scintillation crystal.

FIG. 6a is a schematic top view illustrating the manner in which a scintillation crystal is "tilted" according to the present invention. In FIG. 6a the scintillation crystal 11 drawn in the solid lines represents the position of the scintillation crystal in the non-tilted position. The tilted scintillation crystal 11' is depicted in broken or phantom lines. The vertical axis along which the scintillation crystal 11 is tilted is identified as "v". The angular direction in which the scintillation crystal is tilted about the vertical axis "v" is represented by arrow $\alpha$. The target to be imaged is depicted to indicate how the scintillation crystal is tilted with respect to the target.

FIG. 6b is a schematic top view illustrating the manner in which a scintillation crystal is "pivoted" according to the present invention. In FIG. 6b the scintillation crystal 11 drawn in the solid lines represents the position of the scintillation crystal in the non-pivoted position. The pivoted scintillation crystal 11' is depicted in broken or phantom lines. As depicted in FIG. 6b, pivoting the scintillation crystal essentially requires tilting the scintillation crystal about both the vertical axis "v" and the horizontal axis "h" of the scintillation crystal. The angular direction in which the scintillation crystal is tilted about the vertical axis "v" is represented by arrow $\alpha$. The angular direction in which the scintillation crystal is tilted about the horizontal axis "h" is represented by arrow $\beta$.

It can be seen from comparing FIGS. 6a and 6b that "tilting" the scintillation crystals involves angular positioning about a linear axis, i.e. the vertical axis, while "pivoting" the scintillation crystals involves angular positioning about a pivot point, i.e. the intersection of the vertical and horizontal axis. It is to be understood that the scintillation crystals could be tilted about the horizontal axis rather than the vertical axis.

Pivoting the scintillation crystals allows biaxial alignment and therefore can accommodate the geometry of any given target subject. The pivot angle (measured biaxially) can be the same, opposite, or different for each scintillation crystal as long as the scintillation crystals are positioned, i.e. pivoted, so that they simultaneously receive charged gamma rays emitted from a target subject located between the scintillation crystals in order to identify end points of the line of flight of gamma rays produced by annilation events.

With the cameras positioned in either of the geometries discussed above, photons emerging from the source which enter the scintillation crystals at a shallow angle pass through an extended length of scintillator, thereby increasing the probability of interaction in the scintillator. Because modern cameras have large physical dimensions, this interaction length can be many 10s of centimeters thereby almost guaranteeing that photons emerging from the source will interact in the detectors. Although the principle embodiment of system is designed to use scintillation cameras having NaI(T1) crystals, it should be understood that the concept underlying the invention also applies to cameras using other kinds of scintillators. In particular, performance of the system could be substantially enhanced by using other, higher density, high light output scintillators such as LSO.

In the embodiment depicted in FIGS. 1a and 1b, the detector tilt angle can be varied so that the scintillation crystals are coplanar, or in the other extreme, facing one another. When the scintillation crystals are coplanar, the system has the highest possible sensitivity per slice, because of the great thickness of NaI(T1) (or other scintillator) along the photon flight path. However, with the scintillation crystals coplanar, the system produces only a single tomographic slice equal in thickness to about half the scintillation crystal thickness.

When the scintillation crystals face each other, the system possesses the lowest sensitivity per slice, because the thin dimension of each scintillation crystal is now perpendicular to the photon flight path. However, in this configuration or alignment of the scintillation crystals, the axial extent of the field of view is very large and equal to the width of the cameras' field of view.

The system includes two (or more) cameras connected to a variable, user-selectable tilt or pivot angle mechanism. The tilt or pivot angle can be manually or automatically selected so that the axial field of view can be adjusted to trade sensitivity per slice against axial extent. When the scintillation crystals are coplanar, the device has high sensitivity and high spatial resolution but in only a single tomographic slice. When the scintillation crystals are tilted or pivoted at a shallow angle, the device has an increased axial field of view and a greater number of tomographic slices, but slightly poorer sensitivity per slice. When the cameras are positioned so as to face one another, the device has high resolution, a maximal axial extent and a maximum number of tomographic slices, but reduced slice sensitivity. It is believed that the system would find greatest practical application where the axial extent of the field of view has been adjusted to just span the axial length of the target, thereby maximizing slice sensitivity for that target size. If instead of NaI(T1), a denser, high light output crystal, e.g. LSO, is substituted for NaI(T1), this condition can be relaxed and the tilt or pivot angle can be increased without penalty. Use of such high performance scintillators could improve performance of the described system substantially.

In order to produce tomographic slices from the acquired image data, the endpoints of time coincident interactions in the detector pair must be located and these coordinates used to compute the location of the corresponding coincidence line in a coordinating system fixed in the imaged object, i.e. these lines must be "binned" in a coordinate system fixed in the object.

For illustrative purposes, the following discussion details how image data is managed in the case of two cameras rotating around a stationary subject. It is to be understood that the same principle applies to multiple cameras or to a ring of tilted or pivoted stationary cameras.

A scintillation camera computes the x, y coordinates of the centroid of scintillation events occurring with the cameras field of view. If two 511 keV gamma rays from the same annihilation event interact simultaneously in the two cameras, each camera will output the x, y coordinate of that event along with an energy signal proportional to the energy deposited in the crystal by the photon. By knowing the angular position of the cameras around the subject and the position of each endpoint of the coincidence line in three-dimensional space, the detected position of the coincidence line can to be transformed into a coordinate system at rest in the subject.

Following this transformation, a second transformation is performed in which the coincidence event is "binned" into a "sinogram" at the appropriate projection angle and the proper tomographic slice. The combination of all such events for a full 360 degrees rotation (or 180 degree rotation) of the camera will yield a number of sinograms one for each tomographic slice that can then be reconstructed using standard means to yield the required tomographic images of the source distribution. It should be understood, however, that reconstruction of the target activity distribution is not limited to these "standard" methods. Because the invention is a "volume" or "spatial" imaging device, it is also possible to reconstruct the coincidence data using 3-dimensional methods that substantially increase the sensitivity of the system relative to standard 2-dimensional methods.

Because the system of the present invention involves variable tilt or pivot angles of the cameras, the tilt or pivot angles have to be accounted for when transforming the detected position of the coincidence line into a coordinate system at rest in the subject. Fortunately, accounting for the tilt or pivot angles of the cameras involves a simple geometric calculation.

This binning operation can be performed in real-time or retrospectively depending on count rate. In the two camera imaging system shown in FIG. 3, the required coordinate transformations and binning are carried out during data acquisition and the sinogram is available upon completion of data acquisition. This same technique could be applied when using conventional large field of view cameras as long as the event rates were low enough for the computation to be completed before the next event. If this were not the case, the data could simply be recorded in LIST mode and binned after all the data were collected.

FIG. 2 is a schematic illustration of a data acquisition system used in the paired camera embodiment of the present invention.

The data acquisition system illustrated in FIG. 2 shows cameras 1 and 2 connected to standard NIM amplifiers and stretchers for the purpose of signal conditioning and coincidence detection. Valid (coincident) events are then sent to the illustrated computer system, which includes a standard acquisition board and a processing board, where the position data and rotation angles are digitized. Also illustrated in FIG. 2 is the coincidence circuits which match corresponding coincidence signals received by each of the cameras 1 and 2 to ensure that paired scintillation events in the cameras are used to calculate the coincidence line. Also illustrated in FIG. 2 is the rotator which controls the positioning of the cameras with reference to the subject. As indicated, the angular position of the cameras is provided from the rotator to the computer system. The calculation of the coincidence line is performed according to known algorithms which have previously been applied in systems which involved systems of detectors arranged in a ring. This algorithm has been modified by taking into account the tilt or pivot angle of the scintillation cameras. This further modification merely involves a simple geometric calculation. In this regard, although not illustrated in FIG. 2, information on the tilt or pivot angle of the scintillation cameras could be directly supplied to the data acquisition board of the data acquisition system.

Once the data is acquired, corrections can be applied for spatial variations in sensitivity, scattered radiation, count rate losses, random coincident events, attenuation and other perturbing factors associated with PET. Procedures have been developed for implementing each of these corrections as in other conventional forms of PET imaging.

For purposes of the present invention, it was found that the use of detector shields was helpful to block out activity in other parts of the object outside the imaging field of view. Suitable detector shields 15 which are depicted in FIGS. 1a and 1b include two Pb(lead) slabs which are attached to each rotating camera head. The variable width and orientation of the opening between the slabs allows radiation from the subject to pass into the detectors, yet suppresses radiation emerging from elsewhere in the body. This arrangement will reduce the "single rate" on each detector and improve system count rate performance.

The following non-limiting examples are presented to illustrate features and characteristics of the present invention.

EXAMPLE 1

In this example, a prototype 2-detector small animal imaging system using position sensitive photomultiplier tubes was tested in the single-slice, crystals coplanar PET mode of operation. FIG. 3 illustrates the manner in which the scintillation crystals are arranged to be coplanar. As shown in FIG. 3, both the photomultipliers and their respective scintillation crystals face in the same direction and are positioned on either side of the subject animal across from one another. Each of the scintillation crystals has the same identical geometry. One of the coincidence lines has its endpoints identified and labeled in the scintillator crystals as shown in FIG. 3.

In this mode, the effective entrance aperture was 60 mm by 4 mm (the crystal thickness) with a crystal depth of 50 mm and a center-to-center detector spacing of 25 cm. The intrinsic resolution of these detectors at 511 keV was about 1 mm. FIGS. 4a and 4b illustrate the transverse resolution capability of the prototype device. FIG. 4a is a sinogram acquired with the imaging system in FIG. 3, and FIG. 4b illustrates the in-plane resolution of this system using this sinogram to reconstruct the target activity distribution. Transverse section images through 1 mm (ID) capillary tubes in air revealed a spatial resolution of approximately 2 mm (full width at half maximum, FWHM).

Figure 5:
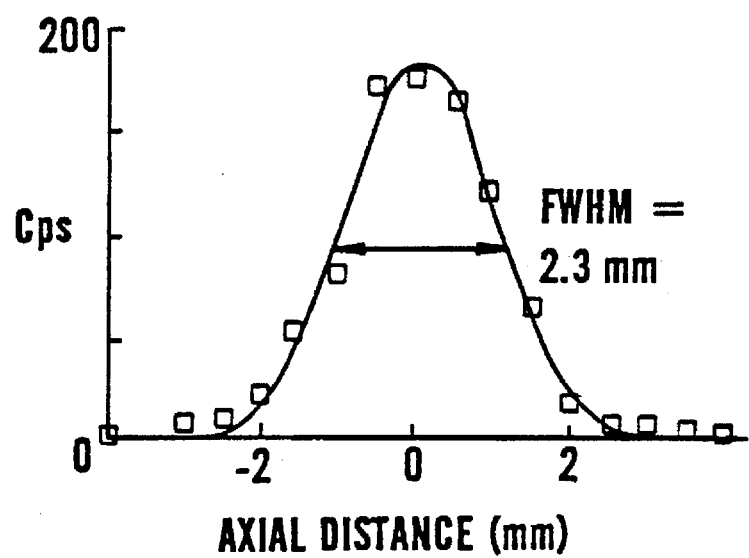
FIG. 5 illustrates the axial slice width of this same system (FIG. 3) when imaging F-18.

FIG. 5a illustrates the axial slice thickness of the detector system shown in FIG. 3. Axial slice thickness measured for this system was 2.3 mm. Point source sensitivity for a source located at the geometric center of the detector pair was 5 cps/microcurie of F-18. This coincidence rate represents a true detection efficiency of approximately 9%.

Based on these measured values, and on the typical design characteristics of modern double or multiple headed scintillation camera systems, it is believed that the PET in-plane spatial resolution of the proposed system would be 4 mm or better for any tilt angle and thus, would be competitive in this respect with any modern PET scanner of conventional "ring" design.

As stated above, principles of the present invention apply to multiple cameras and to a ring of tilted stationary cameras. In addition, by "filling in" two complete, adjacent rings of cameras around a circular aperture, three high resolution slices could be computed, including two "real" slices and one cross slice. Such a system would allow tracer distributions in the brain or other body organs to be visualized with unprecedented spatial resolution, in-plane and axial. Similarly, two coplanar, large field of view scintillation cameras could be rotated around a human subject to produce very high resolution, single slice tomographic images. If the two cameras were placed slightly out of coplanar alignment, image data could be acquired that would allow multiple slices to be constructed along the body axis. Each of these applications could have a substantial impact on the practice of nuclear medicine by allowing a single pair of scintillation cameras to perform single photon planar imaging, single photon emission computed tomography and PET. The cost of such a multi-purpose imaging system would likely be far less than the cost of buying a PET scanner and a single photon system separately. Moreover, the performance of such a system in the single slice mode would, as we have demonstrated, far surpass contemporary multi-crystal PET scanners in spatial resolution.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. An imaging device which comprises:

means defining an imaging target space;

at least two scintillation cameras which are positioned on opposite sides of said imaging target space so as to define one or more matched pairs of scintillation cameras, each of said at least two scintillation cameras including a scintillation crystal;

means for tilting the scintillation cameras of the one or more matched pairs of scintillation cameras and their respective scintillation crystals, so as to maximize coincidence detection sensitivity by adjusting an axial field of view to match an axial extent of a target located in said imaging target space; and means for processing signals generated by said at least two scintillation cameras;

wherein each of said one or more matched pairs of cameras is configured to detect paired gamma rays, emitted simultaneously and in opposite directions from a point of annihilation of a positron in a target within said target space, to thereby define endpoints of a coincidence line passing through said target and connecting said pair of cameras; and wherein each of said one or more matched pairs of cameras is adapted to generate electrical signals, responsive to substantially simultaneous absorption of each of said paired gamma rays by a respective one of said pair of cameras, indicative of said paired gamma rays emanating from a single positron annihilation in said target.

2. An imaging device according to claim 1, wherein said means for tilting comprises means for tilting said one or more matched pairs of scintillation cameras toward and away from one another.

3. An imaging device according to claim 1, further comprising means to rotate said at least two scintillation cameras about said target imaging space.

4. An imaging device according to claim 1, wherein said at least two scintillation cameras include means to shield their respective scintillation crystals from undesired gamma radiation.

5. An imaging device according to claim 1, wherein said signal processing means includes means to compute x and y coordinates of a centroid of scintillation events which occur within a field of view of each of said at least two scintillation cameras.

6. An imaging device according to claim 5, wherein said signal processing means further includes means to compute the location of positron annihilation events which take place in the imaging target space.

7. An imaging device according to claim 1, wherein:

said cameras are configured as non-collimated cameras; and each of said one or more matched pairs of cameras is rotatable around said target space to detect a plurality of paired gamma rays emerging from said target, to thereby define endpoints of a plurality of coincidence lines passing through said target, each of said plurality of coincidence lines connecting said matched pair of cameras.

8. An imaging method which comprises:

providing an imaging target space;

positioning a target capable of emitting gamma rays in said imaging target space;

positioning at least two scintillation cameras on opposite sides of said imaging target space, each of said at least two scintillation cameras including a scintillation crystal which produces an energy signal when a gamma ray is absorbed therein;

tilting the scintillation cameras of a matched pair of scintillation cameras so as to maximize coincidence detection sensitivity by adjusting an axial field of view to match an axial extent of the target;

operating the matched pair of cameras to detect paired gamma rays, emitted simultaneously and in opposite directions from a point of annihilation of a positron in the target within said target space, to thereby define endpoints of a coincidence line passing through said target and connecting said matched pair of cameras;

generating electrical signals, responsive to substantially simultaneous absorption of each of said paired gamma rays by a respective one of said matched pair of cameras, indicative of said paired gamma rays emanating from a single positron annihilation in said target; and processing signals generated by said matched pair of scintillation cameras to produce an image of said target.

9. An imaging method according to claim 8, further comprising rotating said at least two scintillation cameras about said target.

10. An imaging method according to claim 8, wherein said tilting comprises tilting said at least two scintillation cameras toward and away from each other.

11. An imaging method according to claim 8, wherein said at least two scintillation cameras detect end points of a path of flight of paired positron gamma rays emitted from said target and said signal processing comprises determining the path of flight of said paired positron gamma rays relative to the imaging target.

12. An imaging method according to claim 11, further comprising shielding said at least two scintillation cameras from undesired gamma radiation.

13. An imaging method according to claim 8, further comprising incorporating a tracer compound into said imaging target which tracer compound emits positrons.

14. An imaging method according to claim 8, wherein said at least two scintillation cameras are used to perform variable axial aperture positron emission tomography.

15. An imaging method according to claim 8, further comprising the steps of:

rotating said matched pair of cameras around said target space to detect a plurality of paired gamma rays emerging from said target, to thereby define endpoints of a plurality of coincidence lines passing through said target, each said coincidence lines connecting said matched pair of cameras;

wherein said processing step includes producing projections at different angles around said target space corresponding to said plurality of coincidence lines, and developing positron emission tomographic images of a positron distribution within said target in accordance with said projections.

16. An imaging device which comprises:

means defining an imaging target space;

at least two scintillation cameras which are positioned on opposite sides of said imaging target space so as to define one or more matched pairs of scintillation cameras, each of said at least two scintillation cameras including a scintillation crystal;

means for pivoting the scintillation cameras of the one or more matched pairs of scintillation cameras and their respective scintillation crystals, so as to maximize coincidence detection sensitivity by adjusting an axial field of view to match an axial extent of a target located in said imaging target space; and means for processing signals generated by said one or more matched pairs of scintillation cameras;

wherein said cameras of each of said one or more matched pairs of cameras are configured as non-collimated cameras to detect paired gamma rays, emitted simultaneously and in opposite directions from a point of annihilation of a positron in the target within said target space, to thereby define endpoints of a coincidence line passing through said target and connecting said pair of cameras; and wherein each or said one or more matched pairs of cameras is rotatable around said target space to detect a plurality of paired gamma rays emerging from said target, to thereby define endpoints of a plurality of coincidence lines passing through said target, each of said plurality of coincidence lines connecting said pair of cameras.

17. An imaging device according to claim 16 wherein said means for pivoting comprises means for pivoting said one or more matched pairs of scintillation cameras through an angular range in which their respective scintillation crystals can face one another, or be coplanar with one another.

18. An imaging method which comprises:

providing an imaging target space;

positioning a target capable of emitting gamma rays in said imaging target space;

positioning at least two scintillation cameras on opposite sides of said imaging target space, each of said at least two scintillation cameras including a scintillation crystal which produces an energy signal when a gamma ray is absorbed therein;

pivoting the scintillation cameras of a matched pair of scintillation cameras so as to maximize coincidence detection sensitivity by adjusting an axial field of view to match an axial extent of the target;

operating the matched pair of cameras to detect paired gamma rays, emitted simultaneously and in opposite directions from a point of annihilation of a positron in the target within said target space, to thereby define endpoints of a coincidence line passing through said target and connecting said matched pair of cameras;

generating electrical signals, responsive to substantially simultaneous absorption of each of said paired gamma rays by a respective one of said matched pair of cameras, indicative of said paired gamma rays emanating from a single positron annihilation in said target;

rotating said matched pair of cameras around said target space to detect a plurality of paired gamma rays emerging from said target, to thereby define endpoints of a plurality of coincidence lines passing through said target, each of said coincidence lines connecting said matched pair of cameras; and processing signals generated by said matched pair of scintillation cameras to produce an image of said target;

wherein said processing step includes producing projections at different angles around said target space corresponding to said plurality of coincidence lines, and developing positron emission tomographic images of a positron distribution within said target in accordance with said projections.

19. An imaging method according to claim 18, wherein said pivoting comprises pivoting said at least two scintillation cameras through an angular range in which their respective scintillation crystals can face each other or, can be coplanar with each other.

* * * * *